United States Patent [19]
Berg et al.

[11] Patent Number: 5,948,795
[45] Date of Patent: Sep. 7, 1999

[54] BENZOTHIOPENE COMPOUNDS, AND USES AND FORMULATIONS THEREOF

[75] Inventors: David Thompson Berg, Beech Grove; George Joseph Cullinan, Trafalgar; Brian William Grinnell, Indianapolis; Mark Alan Richardson, Bloomington, all of Ind.

[73] Assignee: Eli Lilly and Company, Indianapolis, Ind.

[21] Appl. No.: 08/882,711

[22] Filed: Jun. 25, 1997

Related U.S. Application Data

[60] Provisional application No. 60/021,788, Jul. 15, 1996.

[51] Int. Cl.⁶ .................. A61K 31/445; A61K 31/40; C07D 409/12
[52] U.S. Cl. .................. 514/324; 514/212; 514/422; 540/596; 546/202; 548/525
[58] Field of Search .............. 546/202; 548/525; 540/596; 514/212, 324, 422

[56] References Cited

U.S. PATENT DOCUMENTS

| | | | |
|---|---|---|---|
| 3,594,478 | 7/1971 | Brandstrom et al. | 424/248 |
| 3,598,839 | 8/1971 | Kaltenbronn et al. | 260/330.5 |
| 3,935,231 | 1/1976 | Avar et al. | 260/330.5 |
| 4,133,814 | 1/1979 | Jones et al. | 260/326 |
| 4,418,068 | 11/1983 | Jones et al. | 424/267 |
| 4,654,352 | 3/1987 | Ray | 514/324 |
| 5,175,184 | 12/1992 | Tomiyama et al. | 514/443 |
| 5,254,594 | 10/1993 | Nikura et al. | 514/9.2 |
| 5,472,962 | 12/1995 | Koizumi et al. | 514/233 |
| 5,532,382 | 7/1996 | Carlson et al. | 549/57 |
| 5,595,722 | 1/1997 | Grainger et al. | 424/9.2 |

FOREIGN PATENT DOCUMENTS

| | | |
|---|---|---|
| 0 062 503 | 4/1981 | European Pat. Off. . |
| 0641 791 | 11/1991 | European Pat. Off. . |
| 2 329 271 | 10/1975 | France . |
| 95/34557 | 6/1994 | WIPO . |
| 97/13511 | 10/1995 | WIPO . |

OTHER PUBLICATIONS von Agerer E and Erber S. J. Steroid Biochem. Mol. Biol. 41, 557–562, 1992.
*Chemical Abstracts*, vol. III, No. 9 (Aug. 28, 1989).
*Chemical Abstracts*, vol. 115, No. 5 (Aug. 5, 1991.

*Primary Examiner*—Evelyn Mei Huang
*Attorney, Agent, or Firm*—Gilbert T. Voy

[57] ABSTRACT

Novel benzothiophenes,

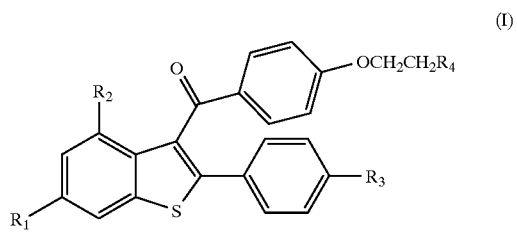

(I)

wherein $R_1$, $R_2$, and $R_3$ are independently —OH, —OCO ($C_1$–$C_6$ alkyl), —O(CO)O($C_1$–$C_6$ alkyl), —OCO—Ar, where Ar is phenyl or substituted phenyl, or —O(CO)O—phenyl; and $R_4$ is N-pyrrolidinyl, N-piperidinyl, or N-hexamethyleneimino, and intermediates thereof, and the uses and formulations thereof, are provided by the present invention.

8 Claims, No Drawings

BENZOTHIOPENE COMPOUNDS, AND USES AND FORMULATIONS THEREOF

This application claims the benefit of U.S. Provisional Application No. 60/021788, filed Jul. 15, 1996.

BACKGROUND OF THE INVENTION

The fibrinolytic system plays a key role in maintaining normal hemostatic balance. A critical factor in this system is plasminogen activator inhibitor I (PAI-1), which reduces the endogenous ability to remove fibrin by inhibiting plasminogen activators such as tissue type plasminogen activator (tPA). Studies have documented that elevations of PAI-1 are associated with increased risk of deep venous thrombosis. Further, elevations in PAI-1 are found in patients suffering from myocardial infarction and septicemia. Because impaired fibrinolytic capacity is associated with increased cardiovascular risk, lowering PAI-1 should result in cardioprotection. In fact, recent studies on the analysis of PAI-1 levels in pre- and post-menopausal women in the Framingham Offspring Study have demonstrated that post-menopausal women have markedly higher PAI-1 levels, which can be reduced to pre-menopausal levels with estrogen therapy. This reduction in PAI-1 effect is believed to contribute to the overall effect of estrogen replacement therapy on the reduced risk of heart disease.

While PAI-1 can be produced in a variety of tissues, substantial levels are secreted by the vascular endothelial cell. The vascular endothelium constitutes a major organ that functions in the regulation of blood coagulation, inflammation and in the exchange of fluids and mediators between the intravascular compartment and parenchyma tissues. As such, the proper function of the endothelium is critical to overall homeostasis. Because PAI-1 can be increased in endothelial cells in response to certain stimuli, including cytokines, it contributes to a dysfunctional state that can result in coagulation defects, local and systemic vascular inflammation, and enhancement in the progression and rupture of atherosclerotic plaque. These effects can further result in conditions including myocardial infarction, deep venous thrombosis, and disseminated intravascular thrombosis.

Because the local control of PAI-1 at the endothelial cell/plasma interface can play a major role in many pathological processes, agents that inhibit the expression of PAI-1 in the endothelium could be useful in treating or preventing conditions such as sepsis, injuries involving major tissue damage and trauma, systemic inflammatory response syndrome, sepsis syndrome, septic shock and multiple organ dysfunction syndrome (including DIC) as well as myocardial infarction, deep venous thrombosis, disseminated intravascular thrombosis, atherosclerotic plaque rupture and its associated sequela.

In addition, tPA (tissue Plasiminogen Activator) is currently administered to patients who have suffered from conditions which place them at risk of detrimental thrombotic events. Exogenously administered tPA has been shown to be effective and is commercially available for treatment of such patients. However, efficacy of this therapy can be limited because PAI-1 inhibits the exogenously given tPA as well as the endogenously derived tPA. Therefore, it would be of great value if an agent were available which could either prolong the half-life or reduce the amount of exogenously administered tPA.

Further, because of the critical role of fibrin in tumor cell biology, agents that modulate PAI-1 may find use as antimetastatic agents.

SUMMARY OF THE INVENTION

This invention provides compounds of formula I

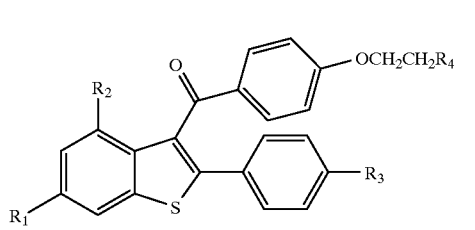

wherein $R_1$, $R_2$, and $R_3$ are independently —OH, —OCO ($C_1$–$C_6$ alkyl), —O(CO)O($C_1$–$C_6$ alkyl), —OCO—Ar, where Ar is phenyl or substituted phenyl, or —O(CO)O—phenyl; and $R_4$ is N-pyrrolidinyl, N-piperidinyl, or N-hexamethyleneimino; or a pharmaceutically acceptable salt or solvate thereof.

Also, included within the scope of the current invention are the compounds of formula II, which are useful in the synthesis of the compounds of formula I:

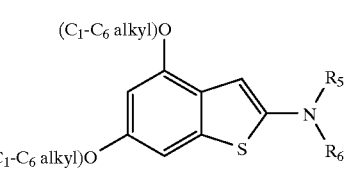

wherein $R_5$ and $R_6$ are independently $C_1$–$C_6$ alkyl.

Further, the compounds of formula IV are provided for the synthesis of the compounds of formula I.

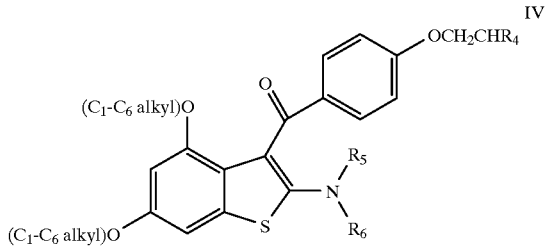

wherein $R_4$, $R_5$, and $R_6$ have their previous meanings.

The present invention relates to methods of using the compounds of formula I in inhibiting PAI-1.

The present invention also relates to pharmaceutical formulations containing compounds of formula I.

DETAILED DESCRIPTION OF THE INVENTION

The current invention concerns the discovery of a select group of novel 2-phenyl-3-aroyl-benzo[b]thiophenes, those of formula I, and their use for inhibiting PAI-1. The methods of use provided by this invention are practiced by administering to a human in need thereof a dose of a compound of formula I, or a pharmaceutically acceptable salt or solvate thereof, that is effective to inhibit PAI-1 or a physiological condition associated with an excess or undesirable activity thereof. The term "inhibit" includes its generally accepted meaning which includes prohibiting, preventing, restraining, and slowing, stopping, or reversing progression, severity, or ameliorating a resultant symptom or effect.

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, iso-pentyl, hexyl, and the like.

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, or tri(chloro or fluoro)methyl. "$C_1$–$C_3$ alkoxy" refers a $C_1$–$C_3$ alkyl group attached through an oxygen bridge such as methoxy, ethoxy, n-propoxy, iso-propoxy.

Compounds of the formula I include the following:

[4,6-dihydroxy-2-(4-hydroxyphenyl)benzo[b]thien-3-yl] [4-[2-(1-pyrrolidinyl)ethoxy]phenyl]methanone dihydrate.

[4,6-dihydroxy-2-(4-hydroxyphenyl)benzo[b]thien-3-yl] [4-[2-(1-hexamethylene)ethoxy]phenyl]methanone dihydrate.

[4,6-dihydroxy-2-(4-hydroxyphenyl)benzo[b]thien-3-yl] [4-[2-(1-piperidinyl)ethoxy]phenyl]methanone dihydrate.

[4,6-diacetoxy-2-(4-acetoxyphenyl)benzo[b]thien-3-y1] [4-[2-(1-piperidinyl)ethoxy]phenyl]methanone dihydrate.

[4-hydroxy,6-acetoxy-2-(4-hydroxyphenyl)benzo[b]thien-3-yl] [4-[2-(1-piperidinyl)ethoxy]phenyl]methanone hydrochloride.

[4,6-dihydroxy-2-(4-acetoxyphenyl)benzo[b]thien-3-yl] [4-[2-(1-piperidinyl)ethoxy]phenyl]methanone.

[4,6-dihydroxy-2-(4-hydroxyphenyl)benzo[b]thien-3-yl] [4-[2-(1-piperidinyl)ethoxy]phenyl]methanone dihydrate.

[4,6-dibenzoyloxy-2-(4-benzoyloxyphenyl)benzo[b]thien-3-yl] [4-[2-(1-pyrrolidinyl)ethoxy]phenyl]methanone hydrochloride.

[4,6-dipentanoyloxy-2-(4-pentanoyloxyphenyl)benzo[b]thien-3-yl] [4-[2-(1-hexamethyleneimino)ethoxy]phenyl]methanone hydrochloride.

[4,6-dibenzyloxyformyloxy-2-(4-hydroxyphenyl)benzo[b]thien-3-yl] [4-[2-(1-piperidinyl)ethoxy]phenyl]methanone hydrochloride.

[4,6-diethyloxyformyloxy-2-(4-ethyloxyformyloxyphenyl)benzo[b]thien-3-yl] [4-[2-(1-pyrrolidinyl)ethoxy]phenyl]methanone.

[4,6-di-(4-methoxybenzoyloxy)-2-(4-(4-methoxybenzoyloxy)phenyl)benzo[b]thien-3-yl] [4-[2-(1-piperidinyl)ethoxy]phenyl]methanone hydrochloride.

[4,6-di-2-propanoyloxy-2-(4-2-propanoyloxyphenyl) benzo[b]thien-3-yl] [4-[2-(1-piperidinyl)ethoxy]phenyl]methanone dihydrate.

[4,6-dihydroxy-2-(4-benzoyloxyphenyl)benzo[b]thien-3-yl] [4-[2-(1-piperidinyl)ethoxy]phenyl]methanone citrate.

A preferred embodiment of this invention is [4,6-dihydroxy-2-(4-hydroxyphenyl)benzo[b]thien-3-yl] [4-[2-(1-piperidinyl)ethoxy]phenyl]methanone dihydrate.

The compounds of formula I are derivatives of the benzo[b]thiophene structure which is named and numbered according to the Ring Index, The American Chemical Society, as follows:

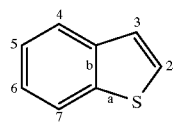

Scheme I illustrates a method for preparing compounds of formula V:

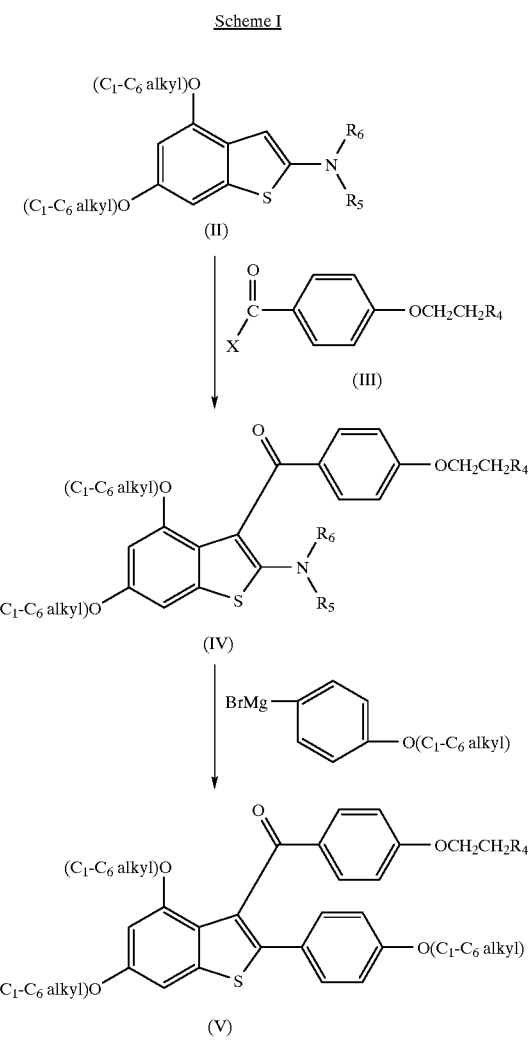

The 4,6-dialkoxy benzo[b]thiophene as its 2-dialkylamino derivative (formula II) where $R_5$ and $R_6$ are independently $C_1$–$C_6$ alkyl, is prepared by the cyclisation of 2-(2,4-dialkylphenyl)-2-hydroxy-N,N-dialkylthioacetamide with a strong acid catalyst, such as methansulfonic acid, at ambient or elevated temperature, approximately 25° to 150° C., in an inert solvent, such as dichloroethane or the like. This reaction is exemplified in Preparation 2.

The thioacetamide may be prepared from the condensation of 2,4-dialkoxybenzaldehyde with N,N-dialkylthioformate, preferred would N,N-dimethylthioformate, and lithium diisopropylamide (LDA) at low temperature, approximately −80° to −50° C., and in an inert solvent such as hexane. This reaction is exemplified in Preparation 1.

The 3-aroyl function bearing the nitrogen-containing side-chain is introduced into an intermediate molecule (formula IV) by reacting 2-(2,4-dialkoxyphenyl)-2-hydroxy-N,N-dialkylthioacetamide with a compound of formula III at elevated temperature (50° to 150° C.) in an appropriate solvent such as toluene, chlorobenzene, or the like. The carbonyl activating moiety of compound III, (X), may be chloro, bromo, a mixed anhydride, or the like. The preferred carbonyl activity moiety is chloro. Compounds of formula III may be facily prepared by methods known in the art such as in U.S. Pat. No. 4,133,814, incorporated herein by reference. An example of this synthesis is illustrated in Preparation 3.

The 2-phenylalkoxy derivative (formula V) is prepared from a compound of formula IV by reaction with 4-alkoxyphenylmagnesium bromide (Grignard reagent) in an inert solvent such as THF, ether, or $CH_2Cl_2$, at a temperature in the range of 0° to 50° C. An illustration of this reaction is given in Preparation 4.

may be prepared by de-protecting (de-alkoxylating) a compound of formula V. Such deprotection methods are taught in the U.S. patent reference, supra, or illustrated in Example 1, below.

The compounds of formula I may also be prepared by variations of other routes (see: Jones, C. D., et al., J. Med. Chem.,1984,27,p. 1057), those routes and appropriate modifications would be apparent and known to those of ordinary skill in the art of organic chemistry.

An alternate synthetic pathway is illustrated in Scheme II, below.

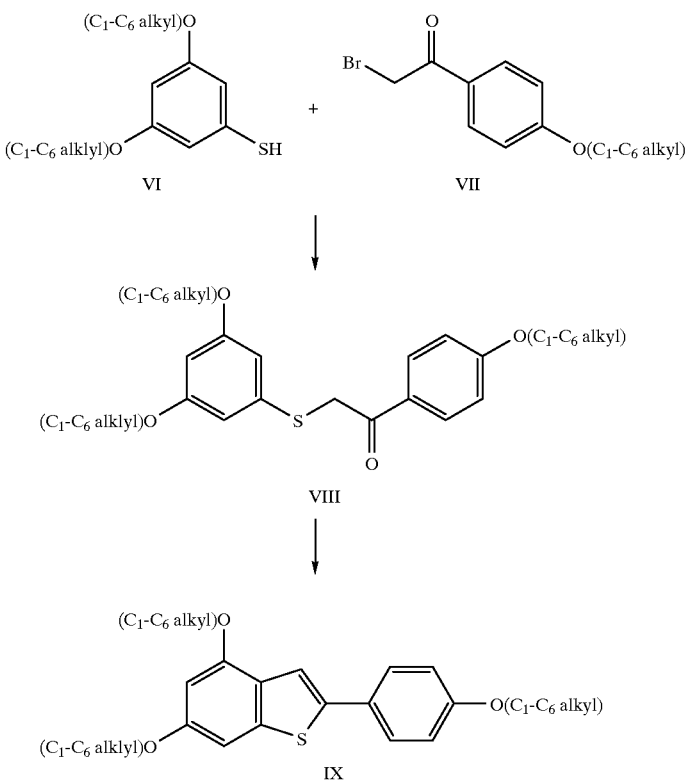

A compound of formula Ia:

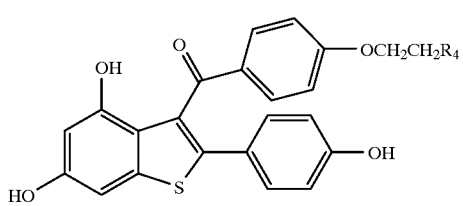

Ia

This reaction sequence begins with the S-alkylation of a thiophenol (VI) with a substituted phenacyl bromide (VII). Preferred substrates for these reactions would the compounds where $(C_1-C_6$ alkyl)O is $CH_3O$—. This reaction is run in the presence of a strong base such as $K_2CO_3$, $Na_2CO_3$, and the like, in inert solvents such as THF, DMF, ether, etc. Although, the reaction will proceed at a variety of temperatures (25° to 125° C.), higher temperatures decrease the time to completion. A preferred temperature would be the reflux temperature of a preferred solvent such as DMF. The reaction is usually complete within one to six hours.

The arylthioether (VIII) is converted to the benzo[b]thiophene (IX) by an acid catalysed, thermal rearrangement. This reaction is usually carried in a high boiling solvent such diphenyl ether, halobenzene, xylenes, etc., preferred would be xylene. The strong acid may be toluenesulfonic acid, sulfuric acid, etc., preferred would be poly-phosphoric acid. The reaction is carried out at about 120° C. and is complete within six to eighteen hours.

The compounds of formula IX may be acylated at the 3-position of the benzothiophene nucleus with an activated carboxyl moieties of a compound of formula III under standard Friedel-Crafts conditions. In general, the acylating conditions would be the use of a Lewis acid such as, $AlCl_3$, $BF_3$, and the like, in an appropriate solvent such as a halogenated hydrocarbon, at temperatures from 0–100° C. The activated carboxyl moieties of the compounds of formula III are acyl halides, mixed anhydrides, and the like, preferred would be the acid chloride. This acylation yields the compounds of formula V.

Other preferred compounds of formula I are prepared by replacing the 6-, -4 and/or -4'-position hydroxy moieties, when present, with a moiety of the formula —O—CO— ($C_1$–$C_6$ alkyl) via well known procedures. See, e.g., U.S. Pat. No. 4,358,593, incorporated herein by reference.

For example, when an —O—CO($C_1$–$C_6$ alkyl) group is desired, a mono-, di-, or trihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The present reactions are carried out at moderate temperatures, in the range from about -25° C. to about 100° C., frequently under an inert atmosphere such as nitrogen gas. However, ambient temperature is usually adequate for the reaction to run.

Acylation of a 6-, -4 and/or -4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R_1$, $R_2$ and/or $R_3$ groups of formula I compounds also may be provided by forming an active ester of the appropriate acid, such as the esters formed by such known reagents such as dicyclohexylcarbodiimide (DCC), acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —O—CO— ($C_1$–$C_6$ alkyl) moieties are carried out in solvents as discussed above. Those techniques which do not produce an acid product in the course of the reaction, of course, do not call for the use of an acid scavenger in the reaction mixture. Other methods are known in the art related to protecting and de-protecting hydroxyl functions (see: e.g., J. W. Barton, "Protective Groups in Organic Chemistry";, J. G. W. McOmie (ed.), Plenum Press, New York, N.Y., 1973, Chapter 2, and T. W. Green, "Protective Groups in Organic Synthesis", John Wiley and Sons, New York, N.Y., 1981, Chapter 7). Further examples of the derivatization of the phenols are illustrated in U.S. Pat. No. 5,393,763, which is incorporated by reference herein.

Preparation 1

N,N-Dimethyl-2-(2,4-dimethoxyphenyl)-2-hydroxythioacetamide

A 110 mL THF solution of lithium diisopropylamide (LDA) ( 80 mmol) was generated from a 1.6 M hexane solution of n-butyllithium (50 mL, 80 mmol) and diisopropylamine ( 11.2 mL, 80 mmol) at -10° C., then cooled to -78° C. A 50 mL solution of 2,4-dimethoxybenzaldehyde (12 g, 72 mmol) and N,N-dimethylthioformamide (6.8 mL, 80 mmol) was cooled to 0° C. and added to the -78° C. LDA solution at a rate keeping the temperature less than -70° C. The reaction mixture was stirred at -75° C. for 2.5 hours, allowed to warm to 0° C., quenched with saturated aqueous $NH_4Cl$, and extracted with EtOAc three times. The EtOAc extracts were combined, washed with brine, dried ($Na_2SO_4$), concentrated, triturated with $Et_2O$/ pet. ether, filtered, and dried in vacuo to give 8.4 g(46% yield) of product: mp 139–140° C.; $^1H$ NMR ($CDCl_3$) d 3.05 (s, 3H, $NCH_3$), 3.50 (s, 3H, $NCH_3$), 3.80 (s, 3H, $OCH_3$), 3.89 (s, 3H, $OCH_3$), 5.19–5.21 (d, 1H, J=7 Hz, OH), 5.72–5.74 (d, 1H, J=7 Hz, CH), 6.43–6.47 (m, 2H, ArH), 7.24(s, 1H, ArH); MS(FD) 255($M^+$). Anal. Calcd for $C_{12}H_{17}NO_3S$: C, 56.45; H, 6.71; N, 5.49. Found: C, 56.64; H, 6.49; N, 5.59.

Preparation 2

2-N,N-Dimethylamino-4,6-dimethoxybenzothiophene

Methanesulfonic acid (2.8 mL, 20 mmol) was added portionwise to a 150 mL $CH_2Cl_2$ solution of N,N-dimethyl-2-(4,6-dimethoxyphenyl)-2-hydroxythioacetamide (2.5 g, 10 mmol) and stirred at ambient temperature for 2 hours. The reaction mixture was poured into saturated aqueous $NaHCO_3$/ice, extracted with $CH_2Cl_2$, the $CH_2Cl_2$ extracts combined, washed with brine, dried ($Na_2SO_4$), and concentrated. The crude product was purified by prep chromatograpy (EtOAc/hexane gradient) to give 1.6 g (70% yield) of product as a clear oil that solidified upon standing: mp 70–73° C.; $^1H$ NMR ($CDCl_3$) 2.97 (s, 6H, $NCH_3$), 3.84 (s, 3H, $OCH_3$), 3.91 (s, 3H, $OCH_3$), 6.09 (s, 1H, ArH), 6.40, (s, 1H, ArH), 6.77 (s, 1H, ArH); MS(FD) 237($M^+$). Anal. Calcd for $C_{12}H_{15}NO_2S$: C, 60.73; H, 6.37; N, 5.90. Found: C, 60.80; H, 6.36; N, 5.84.

Preparation 3

[4,6-Dimethoxy-2-(N,N-dimethylamino)benzo[b]thien-3-yl] [4-[2-(1-piperidinyl)ethoxy]phenyl] methanone A mixture of the 2-dimethylamino-4,6-methoxybenzothiophene (2.9 g, 12 mmol) and the 4-[2-(1-piperidinyl)ethoxy]benzoyl chloride hydrochloride (4 g, 13 mmol) in 200 mL of chlorobenzene was stirred at 100–105° C. for 20 hours, cooled, concentrated, triturated with $Et_2O$, filtered, and dried in vacuo to give the crude hydrochloride salt as a yellow solid. The material was slurried in saturated aqueous $NaHCO_3$, extracted with $CH_2Cl_2$ three times, the $CH_2Cl_2$ extracts combined, washed with brine, dried ($Na_2SO_4$), and concentrated to give 2.7 g(47% yield) of an yellow gum which was used in the next step without further purification. The mass spec and the NMR indicated the gum was the desired product: $^1H$ NMR ($CDCl_3$) 1.44–1.62

(comp, 6H, piperidine), 2.50 (bs, 4H, piperidine), 2.76–2.78 (m, 2H, $CH_2N$), 2.81 (s, 6H, $NCH_3$), 3.41 (s, 3H, $OCH_3$), 3.82 (s, 3H, $OCH_3$), 4.12–4.15 (m, 2H, $OCH_2$), 6.27 (m, 1H, ArH), 6.78 (s, 1H, ArH), 6.86–6.89 (m, 2H, ArH), 7.80–7.82 (m, 2H, ArH); MS(FD) 468($M^+$).

Preparation 4

[4,6-Dimethoxy-2-(4-methoxyphenyl)benzo[b]thien-3-yl] [4-[2-(1-piperidinyl)ethoxy]phenyl]methanone A mixture of magnesium turnings (0.26 g, 10 mmol) and 4-bromoanisole (1.2 mL, 10 mmol) in 10 mL of THF was stirred and sonicated until the magnesium was consumed to give a 1 M THF solution of 4-methoxyphenylmagnesium bromide. A 20 mL THF solution of 2-dimethylamino-4,6-dimethoxybenzothiophene (0.7 g, 1.5 mmol) was stirred at 0° C. while the 1 M THF solution 4-methoxyphenylmagnesium bromide (10 mL, 10 mmol) was added portionwise. The ice bath was removed and reaction mixture was stirred at ambient temperature for 1.5 hours, then recooled and quenched with ice water, extracted three times with $CH_2Cl_2$, the $CH_2Cl_2$ extracts combined, washed with brine, dried ($Na_2SO_4$), concentrated, purified by prep chromatograpy (EtOH/ $CH_2Cl_2$ gradient) and triturated with Et2O/ pet ether, filtered, and dried in vacuo to give 0.7 g(88% yield) of product.: mp 108–110° C.; $^1H$ NMR ($CDCl_3$) 1.44–1.63 (comp, 6H, piperidine), 2.49 (bs, 4H, piperidine), 2.73–2.77 (m, 2H, $CH_2N$), 3.52 (s, 3H, $OCH_3$), 3.75 (s, 3H, $OCH_3$), 3.87 (s, 3H, $OCH_3$), 4.08–4.12 (m, 2H, $OCH_2$), 6.33 (s, 1H, ArH), 6.78–6.88 (m, 4H, ArH), 6.91 (s, 1H, ArH), 7.40–7.43 (m, 2H, ArH), 7.75–7.78 (m, 2H, ArH); MS(FD) 531($M^+$). Anal. Calcd for $C_{31}H_{33}NO_5S$: C, 69.99; H, 6.24; N, 2.53. Found: C, 70.03; H, 6.26; N, 2.63.

Example 1

[4,6-Dihydroxy-2-(4-hydroxyphenyl)benzo[b]thien-3-yl] [4-[2-(1-piperidinyl)ethoxy]phenyl]methanone Dihydrate A 20 mL MeOH solution of 4,6-dimethoxy-2-(4-methoxyphenyl)benzo[b]thien-3yl] [4-[2-(1-piperidinyl) ethoxy]phenyl]methanone (4.8 g, 9 mmol) was stirred at 0° C. while 10 mL of MeOH saturated with HCl was added, then stirred 15 min, concentrated, slurried with $Et_2O$ and concentrated to give the hydrochloride salt as a foam. A 50 mL dichloroethane (DCE) solution of the HCl salt (5 g, 9 mmol) was stirred at 0° C. while a 5.5 M $BCl_3$/DCE solution (7 mL, 38 mmol) was added portionwise, the flask stoppered, and the reaction mixture stirred at ambient temperature for 20 hours. The reaction mixture was quenched at 0° C. with 10 mL MeOH and was poured into saturated aqueous $NaHCO_3$/ice, extracted twice with $CH_2Cl_2$, the $CH_2Cl_2$ extracts combined, washed with brine, dried ($Na_2SO_4$), concentrated, purified by prep chromatograpy (EtOH/$CH_2Cl_2$ gradient), triturated with EtOH/$Et_2O$, filtered, and dried in vacuo to give 2.9 g(63% yield) of product as the dihydrate: mp 151–155° C.; $^1H$ NMR ($CDCl_3$) 1.31–1.55 (comp, 6H, piperidine), 2.21 (bs, 4H, piperidine), 2.55–2.60 (m, 2H, $CH_2N$), 3.30 (bs, 4H, $H_2O$), 4.05–4.11 (m, 2H, $OCH_2$), 6.20 (s, 1H, ArH), 6.65–6.75 (m, 3H, ArH), 6.88–6.94 (m, 2H, ArH), 7.15–7.20 (m, 2H, ArH), 7.55–7.60 (m, 2H, ArH), 9.55 (bs, 1H, ArOH), 9.70 (bs, 2H, ArOH); MS(FD) 489($M^+$). Anal. Calcd for $C_{28}H_{27}NO_5S \cdot 2 H_2O$: C, 63.98; H, 5.94; N, 2.66. Found: C, 63.49; H, 5.70; N, 2.62.

The compounds used in the methods of this invention form pharmaceutically acceptable acid salts with a wide variety of organic and inorganic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit PAI-1, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit PAI-1, or any other use disclosed herein.

Formulations

In the formulations which follow, "Active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

The specific formulations above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 3: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

To demonstrate the utility for the compounds of formula I in inhibiting PAI-1, the following experimental procedure was performed.

Endothelial Cell PAI-1 Assay 96 well tissue culture plates were prepared with $1\times10^4$ human endothelial cells (HUVEC) per well in Clonetics' Endothelial Cell Growth Medium (EGM) supplemented with 2% FBS. Following incubation overnight at 37_C., the medium was replaced with serum-free medium (DMEM/F-12 medium, 20 mM-HEPES, pH 7.5, 50 µg/ml gentamicin, 1 µg/ml human transferrin and 1 µg/ml bovine insulin) with or without compound 1, (where $R_1$, $R_2$, and $R_3$ are hydroxy, and $R_4$ is piperidinyl), and with or without 1 nM IL-1-beta. Following incubation overnight at 37_C., samples of culture medium were assayed for secreted PAI-1 using the Imubind Plasma PAI-1 ELISA (American Diagnostic Inc. #822/1S).

Results

Human umbilical vein endothelial cells (HUVEC) were treated with compound 1 (Example I) concurrent to the induction of PAI-1 with IL-1. In initial experiments with several lots of cells obtained from a commercial supplier (Clonetics), we found that not all lots were responsive to 17-beta estradiol, and were thus not used in experiments to determine the effect of compound 1 on PAI-1 secretion. As shown in Table 1, using an estrogen-responsive line, we observed Compound 1 significantly reduced the induction of PAI-1 by IL-1 at a concentration of 1 nM. These data demonstrate that compound 1 is a potent inhibitor of the induction of PAI-1 from activated endothelial cells and should result in a cardioprotective effect, i.e. reduction in the incidence of cardiovascular events, due to enhancing fibrinolytic potential. Further the positive effect of compound 1 on reducing PAI-1 may provide for acute and chronic uses in conditions where elevated levels are associated with pathology or may be used to prevent such pathological conditions.

TABLE 1

Effect of compound 1 on PAI-1 secretion from human endothelial cells

| Treatment | PAI-1 Induction % of IL-1 Control +/−SE* |
|---|---|
| I1-1 Control | 100 |
| IL-1 & 1 nM Compound 1 | 42 +/−9 |
| IL-1 & 10 nM Compound 1 | 14 +/−5 |

*(drug treated − control)/(I1-1 treated − control) × 100%

We claim:

1. A compound of formula I:

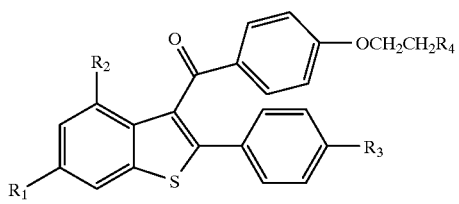

wherein $R_1$, $R_2$, and $R_3$ are independently —OH, —O(CO)O($C_1$–$C_6$ alkyl), —OCO—Ar, where Ar is phenyl or substituted phenyl, or —O(CO)O-phenyl; and $R_4$ is N-pyrrolidinyl, N-piperidinyl, or N-hexamethyleneimino; or a pharmaceutically acceptable salt or solvate thereof.

2. A compound according to claim 1 which is [4,6-dihydroxy-2-(4-hydroxyphenyl)benzo[b]thien-3-yl] [4-[2-(1-piperidinyl)ethoxy]phenyl]methanone dihydrate.

3. A method of inhibiting the induction of PAI-1 comprising administering to a human in need thereof a PAI-1 inhibiting amount of a compound of formula I of claim 1.

4. The method according to claim 3 wherein said compound is [4,6-dihydroxy-2-(4-hydroxyphenyl)benzo[b]thien-3-yl] [4-[2-(1-piperidinyl)ethoxy]phenyl]methanone dihydrate.

5. A pharmaceutical formulation comprising a compound of formula I of claim 1 and one or more diluents, excipients or carriers.

6. The pharmaceutical formulation of claim 5 wherein said compound is [4,6-dihydroxy-2-(4-hydroxyphenyl) benzo[b]thien-3-yl] [4-[2(1 piperidinyl)ethoxy]phenyl] methanone dihydrate.

7. A method of prolonging the half-life of exogenenously administered plasminogen activator by inhibiting the induction of PAI-1 comprising administering to a human in need thereof an effective amount of a compound of formula I of claim 1.

8. A method of inhibiting a pathological condition resulting from, or which is exacerbated by, over induction of PAI-1 comprising administering to a human in need thereof an effective amount of a compound of formula I of claim 1.

* * * * *